United States Patent [19]
Cullinan

[11] Patent Number: 5,985,865
[45] Date of Patent: Nov. 16, 1999

[54] METHODS OF INCREASING SPHINCTER COMPETENCE

[75] Inventor: George Joseph Cullinan, Trafalgar, Ind.

[73] Assignee: Eli Lilly and Company, Indianapolis, Ind.

[21] Appl. No.: 09/063,152

[22] Filed: Apr. 20, 1998

Related U.S. Application Data

[62] Division of application No. 08/779,692, Jan. 7, 1997
[60] Provisional application No. 60/010,771, Jan. 29, 1996.
[51] Int. Cl.$^6$ ............... A61K 31/55; A61K 31/445; A61K 31/40
[52] U.S. Cl. .................. 514/212; 514/324; 514/428
[58] Field of Search ............... 514/212, 324, 514/428

[56] References Cited

U.S. PATENT DOCUMENTS

| | | | |
|---|---|---|---|
| 4,133,814 | 1/1979 | Jones et al. | 260/326.55 |
| 4,418,068 | 11/1983 | Jones | 424/267 |
| 5,567,714 | 10/1996 | Bruns et al. | 514/324 |

FOREIGN PATENT DOCUMENTS

584952A1  3/1994  European Pat. Off. .

OTHER PUBLICATIONS

Isselbacher, et al., "Diseases of the Esophagus", Harrison's Principles of Internal Medicine, (9), 239, (1365–1367).
Harvey, "Gastric Antacids and Digestants" Goodman and Gilman's, The Pharmacologic Basis of Therapeutics, (6), 42, (988–995).
Timiras et al., "The Urinary System", Hormones and Aging, 8, (141–142).
Isselbacher, et al., "Dysuria, Incintinence, and Enuresis", Harrison's Principles of Internal Medicine, (9), 44, (222–223).

*Primary Examiner*—Phyllis G. Spivack
*Attorney, Agent, or Firm*—William R. Boudreaux; James J. Sales

[57] ABSTRACT

A method of increasing gastroesophageal sphincter competence comprising administering to a human in need of treatment an effective amount of a compound having the formula

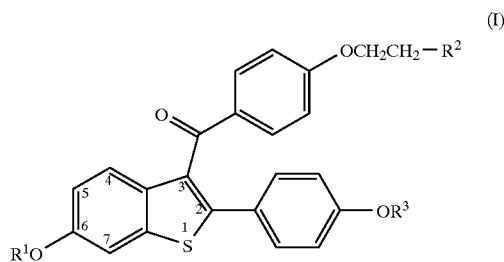

(I)

wherein $R^1$ and $R^3$ are independently hydrogen, —$CH_3$,

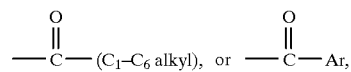

wherein Ar is optionally substituted phenyl;

$R^2$ is selected from the group consisting of pyrrolidino, hexamethyleneimino, and piperidino; or a pharmaceutically acceptable salt or solvate thereof.

2 Claims, No Drawings

5,985,865

METHODS OF INCREASING SPHINCTER COMPETENCE

This Patent Application is a divisional of U.S. patent application Ser. No. 08/779,692 filed on Jan. 7, 1997 which claims the benefit under title 35 United States Code §119(e) of the United States Provisional patent application Ser. No. 06/010,771 having a filing date of Jan. 29, 1996.

BACKGROUND OF THE INVENTION

The current invention relates to the field of medical treatment which is characterized by the absence or diminution of control of sphincters of the gastrointestinal and urinary tracts, especially, that lack of control as seen in patients with hormonal deprivation or imbalance, e.g., post-menopausal women.

Sphincters are structures in the body which regulate the flow of materials between the interior and exterior of the body or between various structures within the body. They function in much the same manner as a gate or valve in a pipe. Sphincters are composed of rings or flaps of either striated or smooth muscle cells between different luminal structures: interior, e.g., between the lower esophagus and upper part of the stomach or between the bladder and the posterior urethra; exterior, e.g., the lower colon and the exterior (the anal sphincter). Sphincters composed of striated muscle and controlled by the sympathetic nervous system can, to some extent, be directed by conscious action, e.g., the external urethral sphincter or the upper esophageal sphincter. Sphincters composed of smooth muscle cells are mainly controlled by the parasympathetic nervous system and are not consciously controlled. Smooth muscle sphincters are controlled by internal signals relating to the conditions in the luminal areas on either side of the sphincter, e.g., food traveling down the esophagus triggers the lower esophageal sphincter to relax or open to the stomach, or pressure in the bladder signals the sphincter to the posterior urethra to open. Opening of a sphincter is accomplished by the relaxation of the muscle's tone. Normally, most sphincters maintain remain closed or contracted in relation to their attached luminal structures, thus shutting off the flow of materials. Failure of sphincters to operate properly may be due to a variety of causes such as an obstruction in the passage, mechanical disruption of the passage by trauma or surgery, improper regulation by signals of the nervous system, or loss of muscle tone due to deterioration of the muscle, often seen in aging or with the loss of homeostatic balance of hormones. (For further details see: "Harrison's Principles of Internal Medicine", 9th Ed., Isselbacher, et al., McGraw-Hill Book Co., NYC, Chap.44, p. 22–3 and Chap. 239, p. 1365–7.)

It is the failure of sphincters due to the loss of hormonal balance and their sequelae which are most germane to the current invention. In particular, the sphincter failure and resulting conditions germane to this invention would be: failure of the posterior urethral sphincter leading to urinary incontinence, failure of the anal sphincter leading to fecal incontinence, and failure of the lower esophageal sphincter leading to gastroesophageal reflux disease.

Urinary incontinence is a common problem with the elderly population with at least 15% incidence. The incidence increases to 60% in patients living in community care facilities (nursing homes). Although the condition is not life-threatening, it is a source of both embarrassment to the patient and a potential problem for the maintenance of proper hygienic care for this population. In economic terms, urinary incontinence represents a substantial cost for the institution providing care for the aged. There are two major types of urinary incontinence which are common to the aged. The first type is stress incontinence which the is inability to hold back micturition when a physical stress is placed in the intraabdominal area, e.g., laughing, coughing, or stressful physical activity. The second type is urge incontinence where the patient can not delay voiding when the bladder is perceived to be full. Both of these types are common in post-menopausal women, especially parous women with weaken or damaged pelvic muscles and ligatures due to child birth. Treatment of this condition may be palliative such as using absorbent undergarments or in severe cases the use of alpha adrenergic blockers such as clonidine. However, agents such as clonidine have substantial cardiovascular side-effects which can make them not useful for chronic administration for urinary incontinence as a sole indication. Much more successful for the chronic treatment urinary incontinence in post-menopausal women is the use of estrogen hormone replacement therapy (HRT).

HRT is not usually indicated for the singular use for treatment of urinary incontinence; however, this is a beneficial effect. However, HRT is plagued with poor patient compliance due to the negative side-effects, e.g., increased risk of uterine cancer with un-opposed estrogen, negative CNS effects when estrogen is combined with progestins, bloating, re-initiation of menses, increased breast cancer risk, etc. Certainly, estrogens are not usually used in males. Therefore, there is a need for better therapies to urinary incontinence, especially in the elderly.

Fecal incontinence occurs in the elderly population in a pattern similar to that seen with urinary incontinence; however, at a much reduced rate. The consequence of patients suffering from this condition can be much worse than those suffering from urinary incontinence in that hygiene becomes a much more serious problem. More care and economic outlay must be used to avoid such problems as infection with this population. Causes for fecal incontinence appear to be similar to those which cause urinary incontinence and therefore, the patient population suffering from this malady is similar, i.e., parous post-menopausal women are the most common suffers. Treatment for this condition is confined to palliative measures, such as absorbent undergarments, frequent changes of garments, and frequent bathing. The use of HRT in post-menopausal women as an effective treatment is not clear, although there is every reason to believe that it has the potential for beneficial effects. Perhaps, the lack of clarity is due to the idiosyncratic nature of this condition or the fact that insufficient data exists because of the relatively few women who will tolerate the negative side-effects of HRT, especially older(70+) post-menopausal women who are the most likely to suffer. It is clear that better therapy in this area would be of benefit. (Further details see; "Hormones and Aging", Ed. Timiras et al., CRC Press, Boca Raton Fla., Chap. 8, p.141–142 and references therein.)

GERD is a condition where the contents of the stomach are spilled up (refluxed) into the esophagus. This condition is often due to a failure of the lower esophageal sphincter to close properly. The consequences of this reflux are annoying to the patient and potentially serious. In milder forms, the patient complains of a burning sensation in the esophagus or heartburn and this often leads to pain, lack of sleep, and loss of productivity. In more serious cases, chronic reflux can lead to ulceration of the esophagus leading to surgical intervention or it is thought to be contributory to the development of esophageal cancer.

People of all ages and sexes can suffer from this malady; However, it is more prevalent in the older population. Anecdotally, women report changes (increase or decrease in symptoms) during menstrual cycles, during pregnancy, and during menopause, yet verification of a linkage between hormonal levels and GERD remains illusive. It is well known that hormones such as estrogen effect other sphincters of similar physiology and it is known that estrogens effect stomach motility and other upper GI functions such as gastric emptying. However, other factors causing failure of the esophageal sphincter, such as herniation of the stomach, hypersensitivity of the esophagus and hyperacidity of the stomach, may cloud a clear understanding of the role of hormones in this condition.

Treatment for GERD consists of mechanical and pharmacologic intervention. Mechanical intervention can be achieved by in several ways, patients who suffer GERD at night can sleep in a more elevated position, thus allowing gravity to keep the stomach's contents from entering the esophagus, obese patients can lose weight, exercise can increase the tone of the supporting muscles, or surgical intervention can be used to repair the effected tissues. Pharmacological intervention consists of lowering the stomach's acidity with antacids or with anticholinergic drugs, such as bethanechol, each or both of these may be effective, but are problematic for long term use due to negative side-effects. New agents by themselves or in addition to known, effective agents would improve current therapies for the treatment of GERD.

The present invention is directed to the discovery that the compounds of the present invention, as defined below, increase sphincter competence.

SUMMARY OF THE INVENTION

This invention provides methods of increasing sphincter competence comprising administering to a human in need thereof an effective amount of a compound of formula I

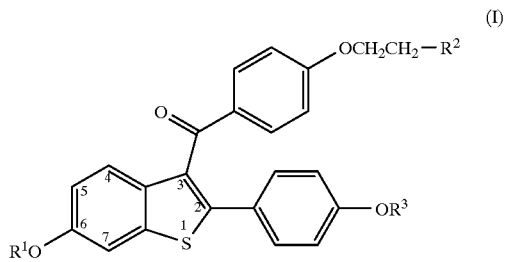

(I)

wherein
$R^1$ and $R^3$ are independently hydrogen, —$CH_3$,

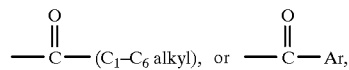

wherein Ar is optionally substituted phenyl;
$R^2$ is selected from the group consisting of pyrrolidino, hexamethyleneimino, and piperidino; and pharmaceutically acceptable salts and solvates thereof.

Also encompassed by the invention are methods for inhibiting urinary and fecal incontinence, and gastroesophageal reflux disease.

DETAILED DESCRIPTION OF THE INVENTION

The current invention concerns the discovery that a select group of 2-phenyl-3-aroylbenzothiophenes (benzothiophenes), those of formula I, are useful for increasing sphincter competence. The methods of use provided by this invention are practiced by administering to a human or mammal in need thereof a dose of a compound of formula I or a pharmaceutically acceptable salt or solvate thereof, that is effective to increase sphincter competence. The present method includes both medical therapeutic and/or prophylactic treatment, as appropriate.

The term "inhibit" includes its generally accepted meaning which includes prohibiting, preventing restraining, and slowing, stopping, or reversing progression, severity, or a resultant symptom or effect.

The term "effective amount" means the amount of compound necessary to inhibit fecal or urinary incontinence, or gastroesophageal reflux disease, or increase sphincter competence, as the case may be.

Raloxifene, a compound of this invention is the hydrochloride salt of a compound of formula I, wherein $R^1$ and $R^3$ are hydrogen and $R^2$ is 1-piperidinyl.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established procedures, such as those detailed in U.S. Pat. Nos. 4,133,814, 4,418, 068, and 4,380,635 all of which are incorporated by reference herein. In general, the process starts with a benzo[b] thiophene having a 6-hydroxyl group and a 2-(4-hydroxyphenyl) group. The starting compound is protected, alkylated or acylated, and deprotected to form the formula I compounds. Examples of the preparation of such compounds are provided in the U.S. patents discussed above. Optionally substituted phenyl includes phenyl and phenyl substituted once or twice with $C_1$–$C_6$ alkyl, $C_1$–$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to increase sphincter competence, inhibit urinary or fecal incontinence, or gastroesophageal reflux disease, according to this invention, will depend upon the severity and nature of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need of treatment from once to about three times each day, or more often as needed to effectively increase sphincter competence, or inhibit urinary or fecal incontinence, or gastroesophageal reflux disease.

It is usually preferred to administer a compound of formula I in the form of an acid addition salt, as is customary in the administration of pharmaceuticals bearing a basic group, such as the piperidino ring. It is also advantageous to administer such a compound by the oral route. For such purposes the following oral dosage forms are available.

Formulations

In the formulations which follow, "active ingredient" means a compound of formula I.

Formulation 1: Gelatin Capsules

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of raloxifene that have been made include those shown below:

Formulation 2: Raloxifene Capsule

| Ingredient | Quantity (mg/capsule) |
| --- | --- |
| Raloxifene | 1 |
| Starch, NF | 112 |
| Starch flowable powder | 225.3 |
| Silicone fluid 350 centistokes | 1.7 |

Formulation 3: Raloxifene Capsule

| Ingredient | Quantity (mg/capsule) |
| --- | --- |
| Raloxifene | 5 |
| Starch, NF | 108 |
| Starch flowable powder | 225.3 |
| Silicone fluid 350 centistokes | 1.7 |

Formulation 4: Raloxifene Capsule

| Ingredient | Quantity (mg/capsule) |
| --- | --- |
| Raloxifene | 10 |
| Starch, NF | 103 |
| Starch flowable powder | 225.3 |
| Silicone fluid 350 centistokes | 1.7 |

Formulation 5: Raloxifene Capsule

| Ingredient | Quantity (mg/capsule) |
| --- | --- |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/tablet) |
|---|---|
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

Formulation 7: Tablets

| Ingredient | Quantity (mg/tablet) |
|---|---|
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60 C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

Formulation 8: Suspensions

| Ingredient | Quantity (mg/5 ml) |
|---|---|
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

As mentioned previously, compounds of formula I can be used as single agents or in combination with known, effective agents. Combination therapy may be in the form a single dosage entity as illustrated above or as separate entities, thus giving the attending physician the greatest latitude of protocols. If a single entity combination is chosen, other beneficial compounds might include, but not be limited to: 0.2 to 2 mg of clonidine for urinary incontinence, 10–50 milliequivalents of antacid for GERD (see: "Goodman and Gilman's, The Pharmacologic Basis of Therapeutics, 6th Ed., Macmillan Publishing Co., NYC, 1980, Chap.42), or 25 mg of bethanecol for GERD. Additionally, these combinations (either as a single entity or as separate entities) may be given at specific time intervals, e.g., after meals or before sleep, as directed by the attending physician.

The following examples would demonstrate the utility of the current invention. These examples are for purposes of illustration and are not meant to limit the use of this invention in any way.

Urinary Incontinence

Trial 1

Fifty women are selected for entrance to the study. Selection criteria is: 50 to 70 years of age, at least one year post-menopausal, in good mental and physical health, and suffering from periods (at least once per week) of stress and/or urge urinary incontinence. Each patient is randomly assigned to either receiving a compound of formula I (treatment group) or placebo (control group). Prior to entry into the study, each patient is asked to record incidences of urinary incontinence for a period of six weeks. The parameters recorded are the number of incidents, time of their occurrence, and some measure of their extent, e.g., were only the undergarments soiled?, how many times, did your incontinence require a change of clothing?, did the bedding get soiled?, could you control the micturation? Did you feel embarrassment or anxiety?, etc.

Twenty-five of the women are given a matched placebo. The other twenty-five are given a compound of formula I, e.g., a formulated capsule containing 60 mg of Raloxifene to be taken once a day. The study continues for three months. During the study, the patients record the same data regarding the number and extent of incidents of urinary incontinence. At the end of the study, the patient's records are analyzed. Due to the idiosyncratic nature of this malady, appropriate, multi-variant analysis would used to analyze the data.

Trial 2

This example is same as Trial 1, with the exception that the control group is given a formulation containing a compound of formula I and an estrogen, once a day.

Trial 3

This study is essentially the same as that in Trial 1, with the exception that the treatment group receives in addition a 0.2 mg dose of clonidine taken orally prior to bed time.

Fecal Incontinence

Trial 4

This study is of the same design as that described in Trial 1 with the exception that the treatment period is extended to one year.

GERD

Trial 5

One hundred post-menopausal women (at least one year menopausal prior to the study initiation) are selected. These patients have the following entrance criterion: suffer from at least one incident of GERD per week or four or more incidents per month and be in otherwise good, general health. The diagnosis that these women are suffering from GERD and not some other malady must be determined by the attending physician. Such diagnosis can be made by techniques known in the medical art, e.g., see: "Harrison's Principles of Internal Medicine", ibid., Chap. 289, p. 1366–7. Each patient is asked to record the number of incidents of GERD and their extent, e.g., When did the incidents occur?, Where was the pain (heartburn)?, What was the patient doing (bending, sitting, lying down)?, Was any material aspirated?, etc.

Fifty patients (control group) are given a matched placebo to be taken orally once a day. The other fifty patients (treatment group) is given a formulation containing a compound of formula I, e.g., a formulated tablet containing 60 mg of Raloxifene, to be taken orally once a day. During the study period, the patients record incidents of GERD and circumstances surrounding these incidents using the same parameters as used in the pre-study period. The study continues for six months. Each patient records are analyzed and compared as to the number and extent of GERD incidents, pre-study versus on-study, using appropriate statistical analysis.

Trial 6

This study would be essentially the same as Trial 5 with the exception that the control group receives in addition 25 mg of bethanecol to be taken orally at bed time. The control group in addition receives a matched placebo to be taken orally bed time.

Trial 7

This study is be essentially the same as that of Trial 5 with the exception that the treatment group would, in addition, receive 20 mL of an antacid such as Maalox® to be taken after each meal and before bed time.

Utility of the compounds of the invention is illustrated by the positive impact displayed by any of the above assays.

We claim:

1. A method for increasing gastroesophageal sphincter competence comprising administering to a human in need thereof an effective amount of a compound having the formula

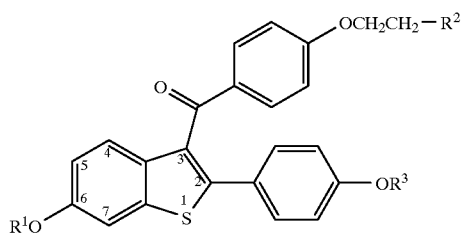

wherein
$R^1$ and $R^3$ are independently hydrogen, —$CH_3$,

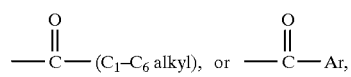

wherein Ar is optionally substituted phenyl;
$R^2$ is selected from the group consisting of pyrrolidino, hexamethyleneimino, and piperidino; or a pharmaceutically acceptable salt or solvate thereof.

2. The method of claim 1 wherein said compound is

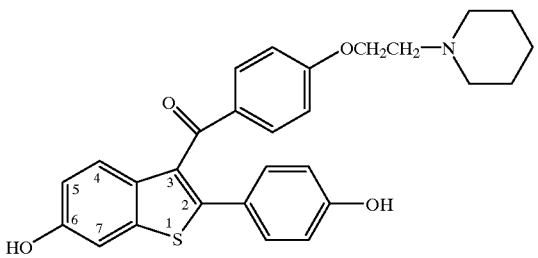

or its hydrochloride salt.

* * * * *